United States Patent [19]

Ravo

[11] Patent Number: 4,969,902
[45] Date of Patent: Nov. 13, 1990

[54] IMPLANTABLE DEVICE

[76] Inventor: Biagio Ravo, Pfizer Inc., 235 E. 42nd St., New York, N.Y. 10017

[21] Appl. No.: 229,938

[22] Filed: Aug. 8, 1988

Related U.S. Application Data

[62] Division of Ser. No. 17,126, Feb. 20, 1987, Pat. No. 4,781,176.

[51] Int. Cl.⁵ .................................................. A61F 2/04
[52] U.S. Cl. ........................................ 623/12; 600/30; 128/DIG. 25
[58] Field of Search ................... 600/29–32; 623/12, 11; 128/DIG. 25, DIG. 26, 899

[56] References Cited

U.S. PATENT DOCUMENTS

| | | | |
|---|---|---|---|
| 3,575,158 | 4/1971 | Summers | 600/30 |
| 3,953,897 | 5/1976 | Chevallet et al. | 623/12 |
| 4,044,401 | 8/1977 | Guiset | 623/12 |
| 4,228,550 | 10/1980 | Salhind | 623/12 |

FOREIGN PATENT DOCUMENTS 2116838 7/1972 France .................................. 623/12

*Primary Examiner*—David J. Isabella
*Assistant Examiner*—David H. Willse
*Attorney, Agent, or Firm*—Peter C. Richardson; Lawrence C. Akers; John L. LaPierre

[57] ABSTRACT

An artificial anus includes a hollow tubular support member, having a cylindrical body portion and a pair of radially-extending flanges at the two opposed open ends of the body portion, and a releasable plug for sealingly closing the hollow support member. The support member is suitable for implantation within an opening in the abdominal wall of the patient, with one of the radially-extending flanges lying upon the dermis or subcutaneous tissue, the other of the flanges lying on the fascia or peritoneum, and the end of the patient's colon received within the support member. Inner and outer layers of at least a portion of the cylindrical body portion are capable of receiving soft tissue ingrowth. A pressure transducer or electrical contact is provided on the support member and connected to an electrode in contact with the patient's skin, so that when the colon becomes pressurized the patient is signalled that the plug should be released. The device can be modified to serve as an artificial bladder or implantable body access device.

5 Claims, 2 Drawing Sheets

IMPLANTABLE DEVICE

This is a division of application Ser. No. 07/017,126 filed on Feb. 20, 1987 now U.S. Pat. No. 4,781,176.

BACKGROUND OF THE INVENTION

In the treatment of certain pathological conditions, such as cancer of the rectum, it is necessary to permanently sever the patient's intestine from the natural anus. At present, medical practice typically requires the performance of a conventional permanent colostomy procedure, in which the end of the remaining intestine is diverted to an artificial opening in the front of the patient's abdomen. For the remainder of his life the patient must collect and dispose his intestinal discharges with the use of an ostomy appliance.

The permanent colostomy procedure is truly life-saving, and permits the patient to resume a pattern of life that is normal in most respects. Nevertheless, the need to permanently use an external ostomy appliance is at best an annoyance and in some cases can lead to significant psychological problems.

Similarly, in the treatment of e.g. bladder cancer it may be necessary to remove the patient's bladder and surgically connect the patient's ureters directly to an intestinal conduit. Urine must consequently be collected and disposed with the use of an appliance such as a urine bag.

Clearly it would be highly desirable and beneficial to provide an implantable device that could simulate the function of the patient's natural anus or bladder and obviate the need to collect and dispose of excrements with ostomy appliances, urine bags, and the like.

SUMMARY OF THE INVENTION

This and other objects are achieved with a novel device of the invention for providing access to the colon through the abdominal wall of a patient and a novel artificial bladder of the invention suitable for implantation in the body of a patient.

The novel colon-access device, which may also be referred to as an artificial anus, comprises a hollow tubular support member having a generally cylindrical body portion adapted to be received within an opening in the abdominal wall and defining a generally cylindrical interior space open at the first and second opposed ends of the body portion to the exterior of the support member, said body portion being adapted to receive the end of the colon within said interior space, and first and second substantially radially-extending flanges adjacent the first and second opposed ends of the body portion, respectively, the first flange being intended to lie upon the dermis or subcutaneous tissue in use and the second flange being intended to lie on the fascia or peritoneum in use; a plug adapted to sealingly close the support member opening to said interior space which is located at the first end of the body portion; means for engaging the plug with the support member adjacent the first end of the body portion to close and seal said support member opening; means for releasing said engaging means to open said support member opening; and means for generating and transmitting to the patient a signal when a predetermined pressure is attained inside the patient's colon in the vicinity of the support member. The novel device can replace the function of the patient's anus and eliminate the need to use ostomy bags or similar external ostomy appliances.

Preferably the aforementioned second flange located adjacent the second end of the cylindrical body portion is capable of being sutured to the adjacent abdominal wall of the patient. It is also preferred that at least a segment of the body portion comprise inner and outer layers of biocompatible polymeric material capable of receiving soft tissue ingrowth, such ingrowth serving, in the case of the inner layer, to bond the end of the patient's colon to the support member and, in the case of the outer layer, to enhance the anchoring of the support member in the abdominal wall of the patient. In one particular preferred embodiment, a major portion of the cylindrical body portion of the support member is comprised of a wall material including inner, middle and outer layers of biocompatible polymeric material, with the inner and outer layers being porous and capable of receiving soft tissue ingrowth and the middle layer being made of a non-porous, water-impermeable material but provided with a plurality of macropores or holes to permit the intergrowth of colon and abdominal wall tissues. In this embodiment the inner, middle and outer layers extend to comprise the second flange of the support member, while only the middle layer (free of macropores or holes) extends to comprise the first flange thereof.

The aforementioned plug may be of any configuration as long as it can be used to sealingly close, and subsequently open, the opening at the outer end of the support member. Thus, the term "plug" is used herein in a very general sense and the plug could be, for example, a threaded cap that can be screwed onto an externally-threaded mouth extending from the outer end of the cylindrical body portion. In one preferred embodiment the plug has a generally disc-like shape, is externally-threaded on its rim, and is adapted to cooperate with an internally-threaded portion of the cylindrical body portion so that it can be screwed into and out of the body portion. Alternatively, the plug may be engaged with and released from the support member by means of a conventional "twist-lock" mechanism. A threaded or "twist-lock" disc or cap may be provided with a handle so that it can be readily rotated in either direction by the patient to open or close the outer opening of the support member.

An important feature of the novel colon access device is a means for generating and transmitting to the patient a signal when a predetermined pressure is attained inside the patient's colon in the vicinity of the support member or when a significant amount of intraluminal content comes into the vicinity of the support member. Preferably, this means includes an electrical circuit which is closed by the activation of a pressure transducer provided on the support member or by the contact of a distended region of the pressurized colon with an electrical contact provided on the support member, and this electrical circuit includes an electrode carried by the first outer flange of the support member in such a manner that it is in contact with the patient's skin in use. Most preferably, of course, the electrode emits only a mild, not unpleasant, signal to the patient's skin when energized. In the embodiment described above wherein the cylindrical body portion of the support member is comprised of three layers, with only the middle layer extending to comprise the first flange of the support member, the electrical circuit is preferably maintained within the non-porous, water-impermeable polymeric material of the middle layer.

The novel artificial bladder of the invention comprises a hollow container comprised of a flexible water-impermeable wall material defining an interior space within the container, with an opening being provided in the wall of said container affording fluid communication between said interior space and the exterior of the container; a first port connected to said container and surrounding said opening, said port being adapted for attachment to the urethra of the patient; means for permitting opening and closing of said first port from the exterior of the artificial bladder to permit the displacement of liquid from the container through the urethra; a second port connected to said container and displaced from said first port and said opening, said second port being adapted for attachment to the end of a ureter of the patient and including a one-way valve permitting fluid flow from the ureter to said container and preventing fluid flow in the opposite direction; and means for generating and transmitting to the patient a signal when a predetermined amount of liquid has been collected in said container. This novel device can replace the function of the patient's bladder and sphincter muscle. In a preferred embodiment, the flexible wall material of the hollow container includes inner and outer layers of biocompatible polymeric material, the latter layer being porous and capable of receiving soft tissue ingrowth and the former being non-porous and water-impermeable. Preferably, the signal generating and transmitting means comprises a liquid level sensor for liquid collected in the hollow container or a pressure transducer included on the container, connected in either case to a skin-contacting electrode of the kind described above with regard to the colon access device of the invention.

The present invention further includes an implantable body access device comprising a hollow container comprised of a flexible wall material defining an interior space within the container, with an opening being provided in the wall of said container affording communication between said interior space and the exterior of the device; a flange connected to said container and extending around said opening, said flange being intended to lie upon the dermis or subcutaneous tissue in use; and means for permitting opening and closing of said opening from the exterior of the device to obtain access to said interior space. This body access device may be used to hold, for example, an insulin infusion pump, a blood sugar detector or the power source for an electromedical device such as a pacemaker.

DETAILED DESCRIPTION OF THE INVENTION

The invention will be described in detail with reference to various preferred embodiments thereof. Reference to these embodiments does not limit the scope of the invention, which is limited only by the scope of the claims. In the drawings:

Figure 1:
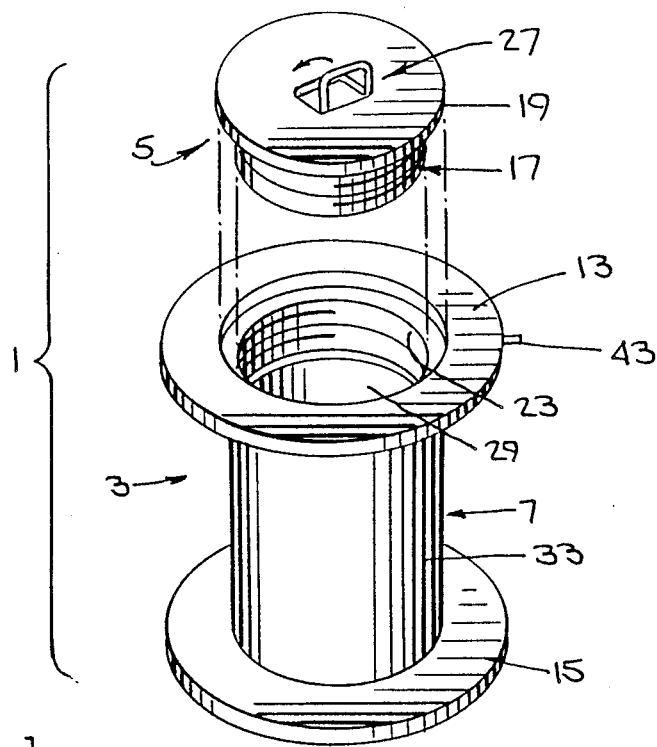
FIG. 1 is an exploded perspective view of a colon access device of the invention.
Figure 2:
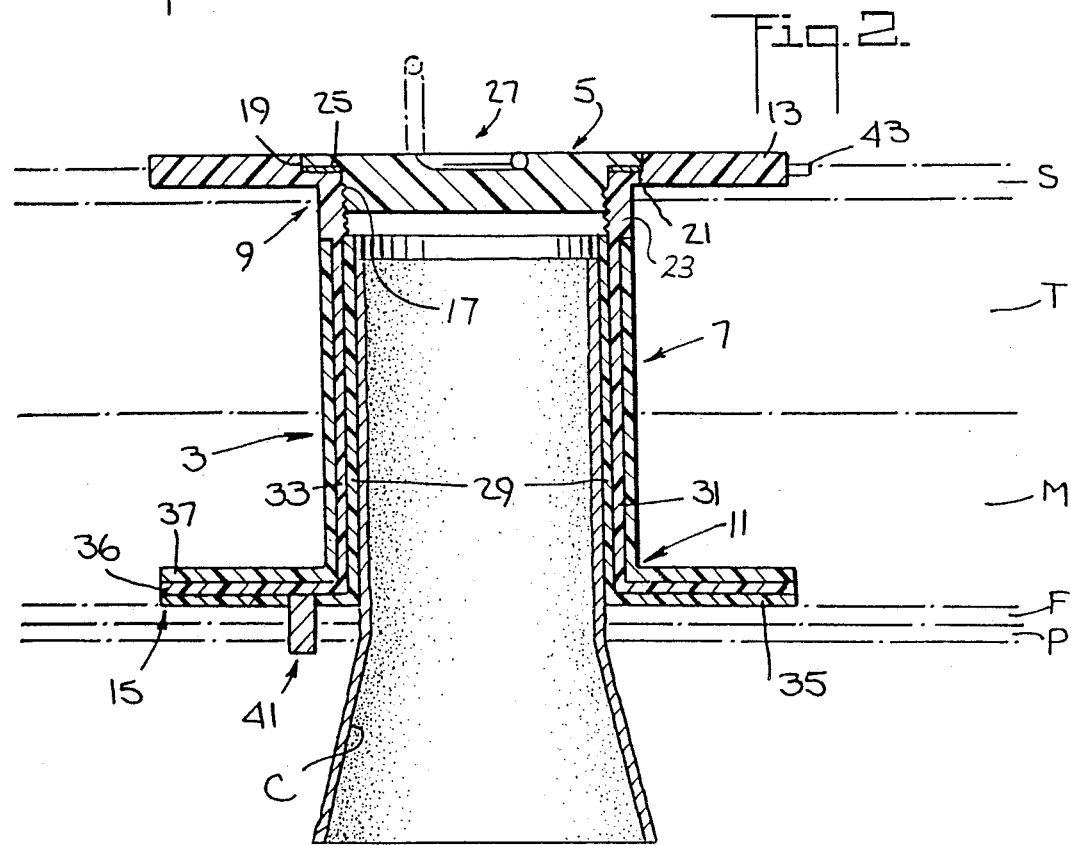
FIG. 2 is a longitudinal sectional view of the device of FIG. 1 shown as implanted in the abdominal wall of a patient.

A device 1 for providing access to the colon through the abdominal wall of a patient is shown in FIGS. 1 and 2. Device 1 includes a hollow tubular support member 3 and a generally disc-shaped plug 5. Support member 3 has a cylindrical body portion 7 defining a cylindrical interior space open at the outer and inner ends 9 and 11, respectively, of body portion 7, a first (outer) radially-extending circular flange 13 located at outer end 9, and a second (inner) radially-extending circular flange 15 located at inner end 11. As shown in FIG. 2, the body portion 7 is adapted to receive the end of the patient's colon C in use.

As used herein in describing a colon-access device of the invention, the terms "inner" and "outer" refer to the orientation of a flange, body portion end, etc., with reference to the intended disposition of the device when implanted in use. In this disposition (see FIG. 2), the body portion 7 is received within an opening in the patient's abdominal wall, which wall includes the four layers of (from outside to inside) the subcutaneous tissue T, muscle M, fascia F and peritoneum P. The inner flange 15 is intended to lie on the fascia or peritoneum in use, with none, some or all of the fascia removed immediately below flange 15 prior to implantation, and the outer flange 13 is intended to lie upon the dermis or subcutaneous tissue in use, with some or all of the patient's skin S removed immediately below flange 13 prior to implantation. Usually, but not necessarily, device 1 will be inserted into the natural anal opening of the patient. However, it is also contemplated that the device could be inserted into an artificial opening created elsewhere in the abdomen.

The rim of the disc-shaped plug 5 includes a threaded smaller diameter inner portion 17 and a non-threaded larger diameter outer portion 19. As shown in FIG. 2, a step 21 is defined between portions 17 and 19. The threaded portion 17 is adapted to cooperate with an internally-threaded outer portion 23 of the cylindrical body portion 7 to close and seal the outer support member opening. Plug 5 can be screwed into body portion 7 until step 21 abuts the support member 3. Preferably, as shown in FIGS. 1 and 2, the outer surface of the support member 3 is countersunk in a configuration complementary with step 21 and rim portion 19 so that when plug 5 is fully advanced within support member 3 the outer (top) surface of the plug is coincident with the outer (top) surface of flange 13. It is also preferred, as shown in FIG. 2, that the plug 5 include a circular gasket 25 forming the inner surface of the step 21. The purpose of this gasket is, of course, to enhance the sealing of the outer opening of the support member.

A foldable handle 27 is provided on the outer surface of the plug 5 to enable the patient to readily rotate the plug in either direction to close or, alternatively, open the outer opening of the support member. Other means, such as a non-foldable handle, can be provided for this purpose.

As shown in FIG. 2, over a major portion of the length of support member 3, the wall material of cylindrical body portion 7 has three layers 29, 31 and 33. The radially innermost layer 29 and the radially outermost layer 33 are both made of a porous biocompatible polymeric material capable of receiving soft tissue ingrowth, e.g. reticulated polyurethane or collagen. The middle layer 31 is made of a non-porous, water-impermeable biocompatible polymeric material such as a silicone elastomer, but may be provided with a plurality of macropores or holes, substantially larger than the pores through layers 29 and 33, to permit the growing together of the soft tissues growing into layers 29 and 33. Preferably, layers 29, 31 and 33 are fused together, for example by adhesive bonding or vulcanization. The middle layer 31 extends beyond layers 29 and 33 to form the entirety of threaded portion 23 of body portion 7. Likewise, the first flange 13 is entirely formed of the same material as, and is preferably in one-piece construction with, the middle layer 31. At the other end of the support member 3, the second flange 15 has three layers 35, 36 and 37 formed of the same materials as, and preferably in one-piece construction with, layers 29, 31 and 33, respectively, of body portion 7.

Plug 5 (except for gasket 25) may be made of any suitable water-impermeable biocompatible polymeric material and is preferably made of the same material as threaded portion 23 of body portion 7. The gasket 25 may be made of a suitable elastomeric material such as rubber or a silicone elastomer.

As one example only, which is not meant to be limiting, the diameter of plug 5 may be about 3.5 cm., the thickness of plug 5 may be about 0.5 cm., and the width (O.D. minus I.D.) of circular flanges 13 and 15 may both be about 1.5 cm.

The device 1 also includes an electrical circuit for generating and transmitting to the patient a mild electrical signal when a predetermined pressure is attained by accumulated excremental matter in the vicinity of the device 1. After the patient receives this signal he may proceed to remove plug 5 and discharge the accumulated matter in a conventional toilet, after which he recloses and reseals the outer support member opening with plug 5. The electrical circuit includes a miniaturized battery power source (not shown), an electrical contact 41 carried by layer 36 of flange 15 and extending through layer 35 and the fascia F and peritoneum P, an electrode 43 carried by flange 13 at the periphery thereof so as to be in contact with the patient's skin S, and thin electrical wire (not shown) connecting the aforementioned elements. The battery and wire are preferably maintained completely within flange 13, middle layer 31 of body portion 7 and layer 36 of flange 15. The electrical contact 41 is designed and positioned in such a manner that when the vicinal region of the colon distends under the predetermined pressure at which the patient is to be signalled to evacuate the colon, the colon comes into contact with contact 41 and thereby closes the electrical circuit.

Alternatively, the electrical contact 41 could be replaced in the circuit by a pressure transducer carried by layer 29 of body portion 7 in direct contact with the end of the patient's colon. This transducer would be set to close the circuit, of course, when the aforementioned predetermined pressure is attained in the colon end. As another alternative the electrical contact 41 could be replaced by a chemical sensor for the accumulated intracolonic content carried by layer 31 of body portion 7 and extending into the intracolonic space. Additionally, it is contemplated that other types of signals than electrical signals emitted by a skin-contacting electrode could be generated and transmitted by a colon access device of the invention, for example audio signals.

In the surgical procedure for implanting the colon access device 1, it is preferable to utilize the natural opening in the patient's anal region; however if desired an artificial opening elsewhere through the abdomen may be created for this purpose. As mentioned above, some or all of the patient's skin S in the area that would be below flange 13 and none, some or all of the patient's fascia F in the area that would be below flange 15 are surgically removed prior to the implantation of device 1. Using an appropriate surgical retractor, the support member 3 is inserted (with the electrical circuit fully operational) into the abdominal opening. After the retractor is disengaged the abdominal wall closes around the support member 3 and contacts body portion 7 and flanges 13 and in the manner shown in FIG. 2. Flange 15 is then sutured around its entire circumference to the adjacent fascia F and peritoneum P. The end of the patient's colon C is then drawn through the inner opening of the support member 3 into the body portion 7 and sutured around its entire circumference, at a position near to the end of layer 29 (see FIG. 2), to all three layers of the body portion 7. The colon is thereby placed into intimate contact with the layer 29 of body portion and, as a result, colon tissue will proceed to grow into layer 29 to further bond the end of the patient's colon to the support member 3. Likewise, abdominal wall tissue will proceed to grow into layer 33 of body portion 7 to enhance the anchoring of support member 3 in the abdominal wall. After the colon C has been sutured to the body portion 7, the plug 5 is fully screwed into the threaded portion 23 of body portion 7 to close and seal the outer opening of support member 3. At this point the device 1 is operational.

Figure 3:
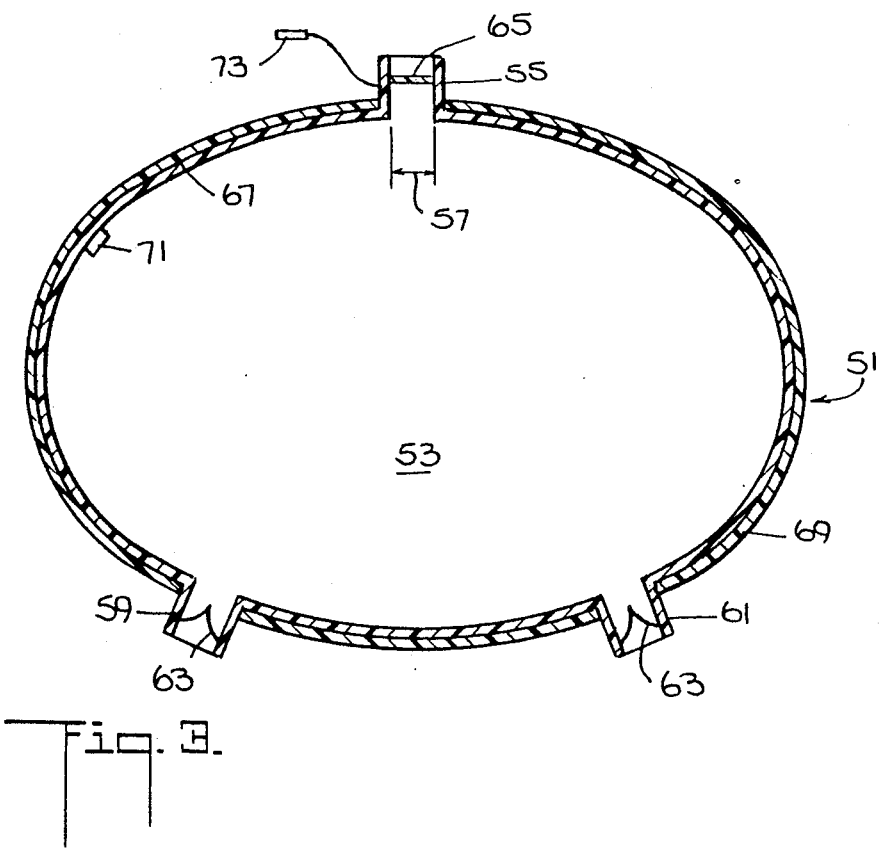
FIG. 3 is a longitudinal sectional view of an artificial bladder of the invention.

An artificial bladder device 51 suitable for implantation in the body of a patient is shown in FIG. 3. Device 51 includes a hollow container 53 comprised of a flexible water-impermeable wall material, and a first port 55 surrounding an opening 57 in container 53. Opening 57 permits fluid communication between the interior space within container 53 and the exterior of the container. The device 51 also includes second and third ports 59 and 61, respectively, both on the other side of container 53 than the first port 55. In use, each of ports 59 and 61 is attached (e.g. by suturing) to the end of a ureter of the patient, while port 55 is attached (e.g. by suturing) to the patient's urethra. A one-way valve 63 is positioned within each of ports 59 and 61; these valves 63 function automatically to permit fluid flow from the ureter to container 53 but not in the opposite direction. One-way valves 63 may be of any conventional type, for example duck-bill check valves. A manually-actuated valve 65 is provided in port 55 to permit the removal of liquid from the container 53, when desired. As shown in FIG. 3, the flexible wall material of container 53 has inner and outer layers 67 and 69, respectively. Inner layer 67 is made of a non-porous, water-impermeable biocompatible polymeric material such as a silicone elastomer. Outer layer 69 is made of a porous biocompatible polymeric material capable of receiving soft tissue ingrowth, e.g. reticulated polyurethane or collagen. The ingrowth of adjacent soft tissues into layer 69 helps to anchor the device 51 in place after its implantation. Preferably, ports 55, 59 and 61 are made of the same material as the inner layer 67. Most preferably, these three ports are in one-piece construction with layer 67.

The manually-actuated valve 65 in first port 55 is closed in its rest condition and open in its actuated condition, and may be of any conventional type. It may be actuated by an electrical, hydraulic or other type of network (not shown). Preferably, an actuation button is implanted just under the patient's skin in the subcutaneous tissue in a position where the patient can readily actuate the network and valve by pressing the button. Implanted manually-actuated valves of this general type are well known in, for example, the penile prosthesis and artificial sphincter fields.

Artificial bladder 51 also includes an electrical circuit for generating and transmitting to the patient a mild electrical signal when a predetermined amount of liquid (i.e. urine entering container 53 through ports 59 and 61) has been collected in the container 53. This circuit includes a miniaturized battery power source (not shown), a pressure transducer 71 carried on layer 67 of container 53, an electrode 73 adapted to be placed in contact with the patient's skin in use, and thin electrical wire connecting the aforementioned elements. When the predetermined amount of liquid has been collected in the container 53, the container becomes sufficiently pressurized to activate the transducer 71, thereby closing the circuit and signalling the patient. The patient can then manually actuate the valve 65 in port 55 to evacuate liquid from the container 53, after which valve 65 returns to its closed condition. As only one alternative, pressure transducer 71 could be replaced by a collected liquid level sensor depending from layer 67.

Figure 4:
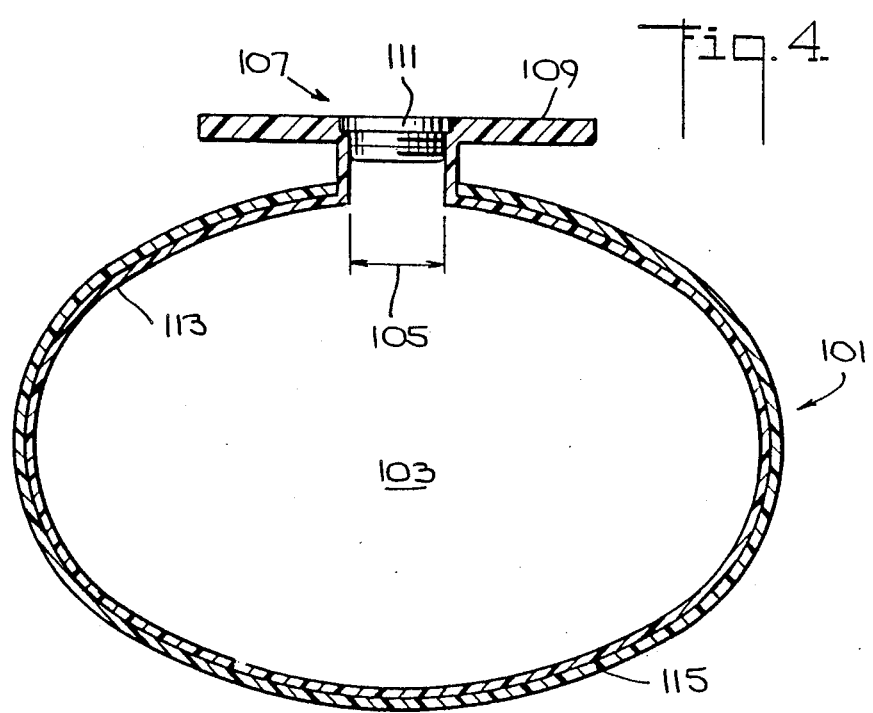
FIG. 4 is a longitudinal sectional view of an implantable body access device of the invention.

An implantable body access device 101 of the invention is shown in FIG. 4. Device 101 includes a hollow container 103 comprised of a flexible wall material having an opening 105. A generally cylindrical port 107 extends around opening 105 and carries a circular radially-extending flange 109 which is intended to lie upon the dermis or subcutaneous tissue of the patient in use. Access to and from container 103 is attained by unscrewing a screw cap 111 which is screwed into port 107 above opening 105 (see FIG. 4) to close the port. Preferably, the flexible wall material of container 103 has inner and outer layers 113 and 115, respectively, having the same characteristics as inner and outer layers 67 and 69 of container 53 of the artificial bladder 51 of FIG. 3. It is also preferred that port 107 and flange 109 be made of the same material as the inner layer 113. Most preferably, port 107 and flange 109 are in one-piece construction with layer 113.

I claim:

1. An artificial bladder suitable for implantation in the body of a patient comprising:
   a hollow container comprised of a flexible water-impermeable wall material defining an interior space within the container, with an opening being provided in the wall of said container affording fluid communication between said interior space and the exterior of the container, said wall material including an inner layer and an outer layer, each layer being separable from one another, with said inner layer being non-porous and water-impermeable and with a substantial portion of said outer layer being non-resorbable, porous, and capable of receiving soft tissue ingrowth to enhance the anchoring of said artificial bladder in the body of the patient;
   a first port connected to said container and surrounding said opening, said port being adapted for attachment to the urethra of the patient;
   means for permitting opening and closing of said first port from the exterior of the artificial bladder to permit the displacement of liquid from the container through the urethra, wherein during said liquid displacement said inner layer separates from said outer layer and collapses inwardly while said outer layer substantially maintains an expanded configuration;
   a second port connected to said container and displaced from said first port and said opening, said second port being adapted for attachment to the end of a ureter of the patient and including a one-way valve permitting fluid flow from the urether to said container and preventing fluid flow in the opposite direction; and
   means for generating and transmitting to the patient a signal when a predetermined amount of liquid has been collected in said container.

2. A device of claim 1 wherein said generating and transmitting means comprises a pressure transducer included on said container.

3. A device of claim 1 wherein said generating and transmitting means includes an electrode capable of being placed in contact with the patient's skin in use, said electrode being adapted to emit a mild electrical signal to the patient's skin when energized.

4. A device of claim 1 further comprising a third port connected to said container and displaced from said first port and said opening, said third port being adapted for attachment to the end of a ureter of the patient and including a one-way valve permitting fluid flow from the ureter to said container and preventing fluid flow in the opposite direction.

5. A device of claim 1 wherein said opening and closing permitting means comprises a manually-actuated valve provided in said first port, said manually-actuated valve being closed in its rest condition.

* * * * *